United States Patent [19]

Reitter

[11] Patent Number: 4,782,821

[45] Date of Patent: Nov. 8, 1988

[54] SHOCK WAVE GENERATOR FOR AN INSTALLATION FOR NON-CONTACTING DISINTEGRATION OF CALCULI IN THE BODY OF A LIFE FORM

[75] Inventor: Josef Reitter, Moehrendorf, Fed. Rep. of Germany

[73] Assignee: Siemens Aktiengesellschaft, Berlin and Munich, Fed. Rep. of Germany

[21] Appl. No.: 57,315

[22] Filed: Jun. 4, 1987

[30] Foreign Application Priority Data

Jul. 14, 1986 [DE] Fed. Rep. of Germany ....... 3623703

[51] Int. Cl.[4] .............................................. A61B 17/22

[52] U.S. Cl. .................................. 128/24 A; 128/328; 367/175

[58] Field of Search ...................... 128/24 A, 328, 804; 367/142, 175; 381/159, 193

[56] References Cited

U.S. PATENT DOCUMENTS 4,665,220 4/1987 Hahn et al. ......................... 128/328
4,669,472 6/1987 Eisenmenger ....................... 128/328
4,674,505 6/1987 Pauli et al. .......................... 128/328

FOREIGN PATENT DOCUMENTS 3312014 11/1985 Fed. Rep. of Germany .
3447440 7/1986 Fed. Rep. of Germany ...... 128/328

*Primary Examiner*—Ruth S. Smith
*Attorney, Agent, or Firm*—Hill, Van Santen, Steadman & Simpson

[57] ABSTRACT

A shock wave generator for an installation for non-contacting disintegration of calculi in the body of a life form has a coil with spirally arranged turns and a membrane formed of an electrically conductive material lying opposite said coil and terminating a space filled with a fluid, the coil being connectable to a high-voltage supply. To assure a high useful life of the membrane without a significant reduction in the efficiency of conversion of electrical energy into shock energy, a distance increased in comparison to regions of low voltage difference is present between the coil and the membrane in regions of high voltage difference between windings of the coil and the membrane.

10 Claims, 1 Drawing Sheet

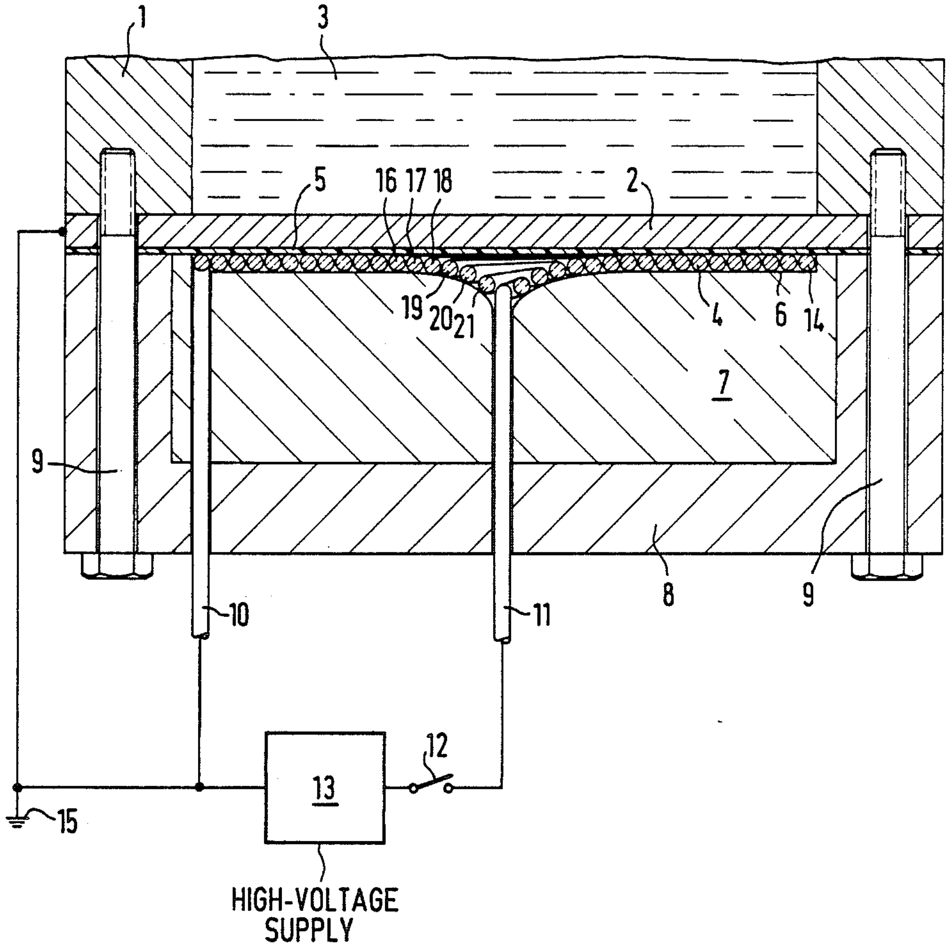
1
3
5
16 17 18
2
19
20
21
4
6
14
7
9
9
8
10
11
12
13
15
HIGH-VOLTAGE
SUPPLY

SHOCK WAVE GENERATOR FOR AN INSTALLATION FOR NON-CONTACTING DISINTEGRATION OF CALCULI IN THE BODY OF A LIFE FORM

BACKGROUND OF THE INVENTION

1. Field of the Invention

The present invention is directed to a shock wave generator for an installation for non-contacting disintegration of calculi in the body of a life form, and in particular to such a shock wave generator having a coil with spirally arranged turns and a membrane of electrically conductive material lying opposite the coil and terminating a space filled with a fluid, the coil being connectable to a high-voltage supply.

2. Description of the Prior Art

A coil and membrane shock wave generator having a membrane arranged parallel to the coil is disclosed in German OS No. 33 12 014. The shock waves are generated by connection of the coil to a high-voltage supply which contains a capacitor charged to a plurality of kilovolts, for example 20 kV. The energy stored in the capacitor then discharges suddenly into the coil, the result being that the coil builds up a magnetic field with extreme rapidity. At the same time, a current is induced in the membrane which is opposite the current flowing in the coil which consequently generates an opposing magnetic field under whose influence the membrane is suddenly moved away from the coil. The shock wave thus generated in the fluid-filled space, for example in a water-filled space, is focussed in a suitable manner onto the calculi, for example kidney stones, situated in the body of the life form, and effecting the disintegration thereof.

In order to achieve the greatest possible conversion of the electrical energy output by the high-voltage supply into shock energy, it is required in the known shock wave generator to attach the membrane optimally close to the coil. Due to the difference in potential necessarily existing between the coil and the membrane, however, this is only possible within limits since a minimum spacing must be observed in order to avoid arcing between the membrane and the coil. Arcing deteriorates the effect of the shock wave generator and leads to damage to the membrane, thereby decreasing its useful life. In the known shock wave generator, therefore, the distance between the membrane and the coil must be selected in the interest of an adequate useful life of the membrane such that an unsatisfactory efficiency is achieved in the conversion of electrical energy into shock energy.

SUMMARY OF THE INVENTION

An object of the present invention is to provide a shock wave generator of this type such that its membrane exhibits a high useful life without a noticeable reduction in the efficiency of the energy conversion being necessary as a compromise.

This object is achieved in accord with the principles of the invention in a shock wave generator wherein an increased interval is present in regions of high voltage difference between the windings of the coil and the membrane, this distance being larger in comparison to regions having low voltage difference. The invention exploits the fact that the high-voltage drops off along the coil, and thus the voltage difference existing between the individual turns of the coil and the membrane changes along an axis of the coil. Accordingly, it is adequate for assuring a high useful life of the membrane if the distance between the turns of the coil and the membrane in those regions in which arcing is most likely due to the great voltage difference present is increased in comparison to regions having a lower voltage difference. A deterioration of the efficiency of the energy conversion thus occurs at most to a limited extent since, in contrast to known shock wave generators, not all turns of the coil are arranged at such a distance from the membrane that dielectric breakdown is avoided given the maximally occurring voltage difference, but rather only those turns in whose region there is in fact a risk of voltage arcing are so arranged A high useful life of the membrane with particularly low influence on the efficiency of the energy conversion can be achieved in an embodiment of the invention wherein the outermost turn of the coil lies at the same voltage as the membrane and the inner turns of the coil are disposed at the increased distance from the membrane. As a result, there is only a slight voltage difference present between the outer turns of the coil, which exert the majority part of the drive energy of the membrane due to their larger diameter, and the membrane, so that these turns can be arranged very close to the membrane The increased distance from the membrane of the inner turns, which exert only a slight part of the drive energy, is without noteworthy influence on the efficiency of the energy conversion in practice A further reduction in the influence on energy conversion is achieved by another feature of the invention wherein the increased spacing present between the turns of the coil and the membrane in regions of high voltage difference continuously decreases toward regions of lower voltage difference. This insures that only that spacing required in order to avoid arcing, and thus to assure an adequate useful life of the membrane, is in fact present in regions of high voltage difference between the individual turns of the coil and the membrane.

In order to avoid hazards to the life form to be treated as well as to the operating personnel, the invention provides that the membrane lies at grounded potential, assuring that no high-voltage is adjacent to the fluid situated in the space, since this fluid could potentially come into contact with the life form or, with the operating personnel.

The turns of the coil may be arranged on a seating surface of an insulator, with the seating surface shaped in accord with the distance respectively required between the turns and the membrane. A reliable observation of this distance is thus guaranteed.

DESCRIPTION OF THE DRAWINGS

An exemplary embodiment of the invention is shown in the drawing whose single figure shows a longitudinal section through a shock wave generator of the invention.

DESCRIPTION OF THE PREFERRED EMBODIMENTS

The shock wave generator of the invention has a housing 1 which contains a space 3 filled with fluid and terminated by a membrane 2 formed of electrically conductive material. A coil 4 having spirally arranged turns is disposed opposite the membrane 2. An insulating foil 5 is arranged between the membrane 2 and the coil 4. The turns of the coil 4 are arranged on a seating surface 6 of an insulator 7 which is received in a cap or cover 8. The membrane 2, the insulating foil 5 and the cap 8 containing the insulator 7 together with the coil are secured to the housing 1 with screws 9. For fixing the coil 4 to the seating surface 6 of the insulator 7, the space situated between the insulator foil 5 and the seating surface 6 of the insulator 7 is filled with an electrically insulating casting resin which is not shown for reasons of clarity. Terminals 10 and 11 emerge toward the outside through bores in the insulator 7 and in the cap 8, by which the coil 4 is connectable via a suitable switch means 12 to a schematicaly illustrated high-voltage supply 13 which emits a current surge to the coil 4, causing the membrane 2 to be suddenly repelled from the coil 4, leading to the formation of a shock wave in the fluid in the space 3. As a consequence of the high-voltage at the coil 4, voltage differences occur between the membrane 2 and the individual turns of the coil 4.

It is provided that an increased distance is present between the coil 4 and the membrane 2 in regions of great voltage difference between the turns of the coil 4 and the membrane 2 in comparison to regions of low voltage difference. In the case of the shock wave generator of the invention as shown, as may be seen from the figure, the outermost turn 14 of the coil 4 lies at the same potential as the membrane 2, namely at ground potential, so that a high voltage difference is present between the inner turns 16 through 21 of the coil 4 and the membrane 2. Consequently, the turns 16 through 21 are arranged at a greater distance from the membrane 2 than the outer turns of the coil 4 exhibiting a low voltage difference with respect to the membrane 2.

The distance of the turns 16 through 21 from the membrane 2 likewise decreases continuously, in the same way as the decrease in the voltage difference. The seating surface 6 of the insulator 7 is thus shaped in accord with the respective distance required between the turns 16 through 21 and the membrane 2.

A shock wave generator having a planar membrane 2 has been shown in the exemplary embodiment, however, it is also possible to fashion shock wave generators having differently shaped membranes, for example spherically shaped membranes, in accord with the invention.

Additionally, within the framework of the invention, the innermost turn of the coil, for example, can be at a positive potential, the outermost turn of the coil can be at a negative potential, and the membrane can be at a potential therebetween. Both the inner and the outer turns of the coil would then exhibit an increased distance from the membrane.

Although modifications and changes may be suggested by those skilled in the art it is the intention of the inventor to embody within the patent warranted hereon all changes and modifications as reasonably and properly come within the scope of his contribution to the art.

I claim as my invention:

1. A shock wave generator operable at a high voltage comprising:

a housing have a volume containing a shock wave transmitting medium, said volume terminating on one side with a membrane consisting of electrically conductive material;

a high voltage source for providing said high voltage;

a coil arranged opposite to said membrane outside said volume;

switch means for connecting said coil to said high voltage source such that the high voltage drops along said coil, said coil and said membrane thereby having a varying voltage difference therebetween with at least one region of said coil having a higher voltage difference with respect to said membrane than another region of said coil; and means for supporting said coil relative to said membrane so that said one region of higher voltage difference is disposed a farther distance from said membrane than said other region.

2. A shock wave generator as claimed in claim 1, wherein said coil has spirally arranged turns with an outermost turn and a plurality of inner turns terminating short of said outermost turn, and wherein said outermost turn of said coil is at the same potential as said membrane, said inner turns of said coil comprising said at least one region of said coil disposed at said farther distance from said membrane.

3. A shock wave generator as claimed in claim 2, wherein said coil has an innermost turn with the voltage difference continuously decreasing from said innermost turn to said outermost turn, and wherein said varying distance between said coil and said membrane continuously decreases in said one region starting from said innermost turn and terminating before said outermost turn.

4. A shock wave generator as claimed in claim 1, wherein said membrane is at ground potential.

5. A shock wave generator as claimed in claim 1, wherein said means for supporting said coil consists of insulating material and has a seating surface on which said coil is disposed, said seating surface having a shape selected for varying the distance between said coil and said membrane.

6. A shock wave generator as claimed in claim 1, wherein said membrane is planar.

7. A shock wave generator operable at a high voltage comprising:

a housing having a volume containing a shock wave transmitting medium, said volume terminating on one side with a membrane consisting of electrically conductive material;

a high voltage source for providing said high voltage;

a spirally wound coil arranged opposite to said membrane and having an innermost turn and an outermost turn, and a region adjacent said innermost turn consisting of a plurality of turns and terminating short of said outermost turn, said outermost turn of said coil being electrically connected to said membrane;

switch means for connecting said coil to said high voltage source such that said high voltage drops along said coil and said coil and said membrane thereby have a varying voltage difference therebetween which is highest at said innermost turn of said coil and lowest at said outermost turn of said coil and which varies continuously therebetween; and means for supporting said coil with respect to said membrane such that said innermost turn of said coil is supported at a farthest distance from said membrane and said outermost turn of said coil is disposed a closest distance from said membrane, with the distance between said coil and said membrane varying continuously in accord with said varying voltage difference for said turns in said region adjacent said innermost turn.

8. A shock wave generator as claimed in claim 7, wherein said membrane is at ground potential.

9. A shock wave generator as claimed in claim 7, wherein said means for supporting said coil consists of insulating material.

10. A shock wave generator as claimed in claim 7, wherein said membrane is planar.

* * * * *